(12) United States Patent
Irwin et al.

(10) Patent No.: US 9,855,403 B2
(45) Date of Patent: *Jan. 2, 2018

(54) SELF-COILING STYLET NEEDLE DEVICE

(71) Applicant: Cook Medical Technologies LLC, Bloomington, IN (US)

(72) Inventors: Nathaniel A. Irwin, Bloomington, IN (US); Michael S. Clancy, Limerick (IE); Darach McGrath, County Tipperary (IE); Ciarán Toomey, County Cork (IE); Ronan Leahy, County Limerick (IE); Fionan Keady, County Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/055,232

(22) Filed: Oct. 16, 2013

(65) Prior Publication Data

US 2014/0114254 A1   Apr. 24, 2014

Related U.S. Application Data

(60) Provisional application No. 61/716,002, filed on Oct. 19, 2012.

(51) Int. Cl.
*A61B 5/00* (2006.01)
*A61M 25/00* (2006.01)
(Continued)

(52) U.S. Cl.
CPC ..... *A61M 25/0102* (2013.01); *A61B 10/0233* (2013.01); *A61B 10/04* (2013.01); *A61B 17/3478* (2013.01); *A61B 2010/045* (2013.01)

(58) Field of Classification Search
CPC ....................................................... A61B 5/00
(Continued)

(56) References Cited

U.S. PATENT DOCUMENTS 5,125,906 A * 6/1992 Fleck ............................ 604/171
5,221,269 A * 6/1993 Miller et al. .................. 604/528
(Continued)

FOREIGN PATENT DOCUMENTS

WO    WO 2011/109792 A1    9/2011

OTHER PUBLICATIONS

Unknown author, "Metal sheath 21G TBNA aspiration needle with side-hole," Olympus, Products Overview, published prior to at least Oct. 16, 2013, 1 page.
(Continued)

*Primary Examiner* — May Abouelela
(74) *Attorney, Agent, or Firm* — Brinks Gilson & Lione

(57) ABSTRACT

A medical device includes an elongate single-wire memory-metal body with a complete length that includes a proximal stylet length, an intermediate self-coiling stylet length, and a distal stylet length that is generally straight and non-self-coiling. The moment of force of the self-coiling stylet length is less than the moment of force of the medical endoscopy needle that is resistant to the stylet's self-coiling force. The device may further include being incorporated into an endoscopy needle system where the single-wire stylet body is disposed through a lumen of a medical endoscopy needle.

15 Claims, 10 Drawing Sheets

(51) Int. Cl.
*A61M 25/01* (2006.01)
*A61B 10/02* (2006.01)
*A61B 10/04* (2006.01)
*A61B 17/34* (2006.01)

(58) Field of Classification Search
USPC .......................... 600/573, 585; 604/523, 528
See application file for complete search history.

(56) References Cited

U.S. PATENT DOCUMENTS

| | | | |
|---|---|---|---|
| 5,366,444 A * | 11/1994 | Martin ........................ | 604/159 |
| 5,599,300 A * | 2/1997 | Weaver et al. .............. | 128/898 |
| 5,666,968 A * | 9/1997 | Imran et al. ................. | 600/585 |
| 5,730,741 A * | 3/1998 | Horzewski et al. ............. | 606/1 |
| 5,846,210 A * | 12/1998 | Ogawa et al. ................ | 600/585 |
| 5,891,058 A * | 4/1999 | Taki et al. ..................... | 600/585 |
| 5,944,701 A * | 8/1999 | Dubrul ........................ | 604/264 |
| 6,017,340 A * | 1/2000 | Cassidy ................. | A61B 18/14 606/110 |
| 6,139,540 A * | 10/2000 | Rost et al. .................... | 600/585 |
| 6,308,090 B1 * | 10/2001 | Tu et al. ....................... | 600/374 |
| 6,602,250 B2 * | 8/2003 | Karpiel et al. ................. | 606/45 |
| 7,374,564 B2 * | 5/2008 | Brown ......................... | 606/127 |
| 7,721,742 B2 * | 5/2010 | Kalloo et al. ................. | 600/115 |
| 7,963,947 B2 * | 6/2011 | Kurth et al. .............. | 604/164.08 |
| 8,021,371 B2 * | 9/2011 | Ishida et al. ................. | 606/108 |
| 8,298,160 B2 * | 10/2012 | Oslund et al. ................ | 600/585 |
| 8,641,748 B2 * | 2/2014 | Hebert et al. ................ | 623/1.11 |
| 2002/0099309 A1 * | 7/2002 | Beger et al. ................. | 600/585 |
| 2004/0019302 A1 * | 1/2004 | Williams et al. ............. | 600/585 |
| 2004/0073141 A1 * | 4/2004 | Hartley et al. ................ | 600/585 |
| 2004/0116878 A1 * | 6/2004 | Byrd ...................... | A61N 1/056 604/263 |
| 2006/0167416 A1 * | 7/2006 | Mathis ............... | A61B 10/0275 604/164.01 |
| 2007/0185413 A1 * | 8/2007 | Asai et al. ..................... | 600/585 |
| 2007/0270679 A1 * | 11/2007 | Nguyen et al. .............. | 600/373 |
| 2008/0015471 A1 * | 1/2008 | Skujins et al. ................ | 600/585 |
| 2008/0086854 A1 | 4/2008 | Boyd et al. | |
| 2009/0227899 A1 * | 9/2009 | Ishida et al. ................. | 600/585 |
| 2010/0228152 A1 * | 9/2010 | Fisher et al. ................. | 600/585 |
| 2012/0041422 A1 * | 2/2012 | Whiting et al. .............. | 604/528 |

OTHER PUBLICATIONS

International Search Report and Written Opinion of the International Searching Authority for International Application No. PCT/US2013/065212, dated Jan. 21, 2014, 11 pages.

* cited by examiner

SELF-COILING STYLET NEEDLE DEVICE

CROSS-REFERENCE TO RELATED APPLICATIONS

This application is a non-provisional application which claims priority to U.S. provisional application Ser. No. 61/716,002, filed Oct. 19, 2012, which is incorporated by reference herein in its entirety.

TECHNICAL FIELD

Embodiments disclosed herein generally relate to a medical endoscopic needle and stylet system. More particularly, the disclosed embodiments relate to a self-coiling stylet.

BACKGROUND

Fine needle aspiration (FNA) and fine needle biopsy are diagnostic biopsy procedures used to obtain a sample from a target site in a patient body. A fine needle (e.g., 19-gauge to 25-gauge) is directed to a target site, and suction is applied to the proximal end of a lumen of the needle to aspirate cells through its distal end. The procedure typically is far less invasive than other biopsy techniques, whether performed percutaneously (e.g., to sample a suspected breast tumor or subcutaneous lesion) or endoscopically (e.g., to sample a suspected cholangiocarcinoma via a duodenoscope). Moreover, advances in endoscopic ultrasound (EUS) technology have helped physicians and patients by providing enhanced ability of a physician to visualize a biopsy needle to obtain a sample of material from a target site without requiring an open incision or use of large-bore needles and/or percutaneous trocars.

In order to provide desirable pushability and trackability for these small-bore sample-collection needles, and to prevent inadvertent (e.g., early and/or late) collection of tissue in one or more distal needle openings, a stylet is typically provided through the length of the needle lumen. After the distal end opening(s) of the needle is/are directed to a target location via a medical endoscope such as a duodenoscope or other minimally-invasive endoscope device, the stylet is withdrawn and a syringe or other modality is attached to the proximal needle end for generating vacuum through the needle lumen to facilitate sample collection by drawing sample material into the distal end opening(s) of the needle. Stylet-management may pose challenges during such procedures.

Specifically, a nurse or other person assisting the physician conducting the endoscopic sample collection must typically use both hands to withdraw the stylet from the needle lumen. Because the stylet may be nearly 2 meters in length and is non-sterile after having been inside the patient, it is usually wound up by nurse as it is withdrawn. However, the default configuration/orientation of existing stylets is generally straight, which is to say that their default configuration is to lie along an uncurved line in all longitudinal planes. As such, stylets are biased to become unwound. This can pose a sharps injury risk due to a sharp distal tip when a stylet springs loose from a wound-up position, and/or it can become contaminated by contacting other non-sterile surfaces. For this reason, the nurse must often clip or otherwise secure the wound-up stylet. In the event that the stylet must be reintroduced into the needle, both hands of the nurse are required to control unwinding and to feed the distal stylet portion back into the needle lumen. If the wound-up stylet escapes the clip or other constriction, it may contact the floor or another contaminating surface and have to be replaced by a sterile stylet—increasing procedure time and expense.

Thus, it may be desirable to provide a stylet configuration that will reduce procedure time, reduce the manual manipulation required during a stylet/needle procedure such as endoscopic sample collection (e.g., FNA, FNB), and that will reduce other risks associated with loss of stylet control during such a procedure.

BRIEF SUMMARY

The needs described above are met by certain embodiments of the presently described and claimed invention. In one aspect, embodiments disclosed herein include a medical endoscopy sample-collection system including a single-wire memory metal stylet disposed through a needle lumen, as well as methods for using that system. In another aspect, embodiments disclosed herein may include a single-wire memory metal stylet with a self-coiling intermediate length. Additionally, in certain embodiments, a self-coiling single-wire memory metal stylet may include particular patterns of self-coiling that prevent tangling and enhance the ease of manipulating the device.

DETAILED DESCRIPTION

Figure 1:
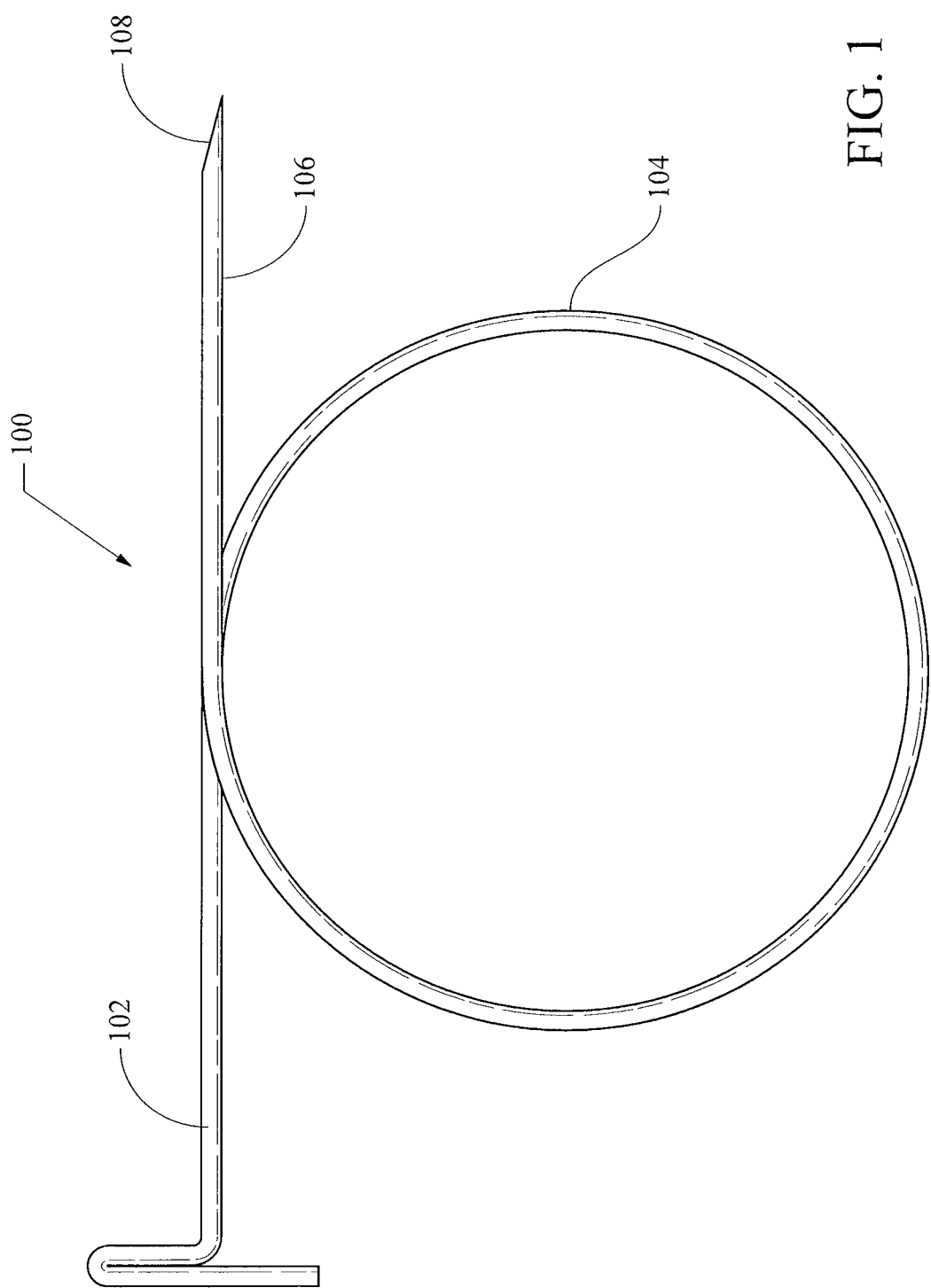
FIGS. 1-1H each show a self-coiling single-wire-body stylet embodiment.

Various embodiments are described below with reference to the drawings, in which like elements generally are referred to by like numerals. The relationships and function(s) of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The terms "proximal" and "distal" are used herein in the common usage sense where they refer respectively to a handle/doctor-end of a device or related object and a tool/patient-end of a device or related object.

As used herein, the term "moment of force" refers to the tendency of a force to coil, twist, or rotate an object and/or to resist coiling, twisting, or rotation. Specifically, the term is used to refer to the self-coiling force of a memory-metal stylet along a length thereof and to refer to the resistance of a needle to that self-coiling force along a corresponding length thereof. The term "single-wire" refers to a structure that, along the distal operating longitudinal length thereof, includes only a single lengthwise wire with no other parallel, coaxial, or other wires (e.g., differentiating it from the braided, coaxially coiled, and other wire structures used in guidewires, catheter bodies, and other wire-based structures). In many preferred embodiments of the presently disclosed stylets and systems, the moment of force of a self-coiling shape-memory material portion of the stylet (that disposes it to coil) will be less than the moment of force of a medical tubular device such as a needle, catheter, or other device (that resists coiling). As such, and depending upon specific configurations, the self-coiling stylet portion will impose little or no curvature on a medical tube device in some embodiment, while providing a greater degree of curvature to the tube device in other embodiments—but still far less curvature than the stylet when unconstrained.

One embodiment of a self-coiling stylet is described with reference to FIG. 1, which shows a stylet 100. The stylet 100 is constructed with an elongate single-wire memory-metal (or other shape-memory material) body with a complete length that includes a proximal stylet length 102, an intermediate self-coiling stylet length 104 including at least one coiled loop—which may include a plurality of coiled loops, and a distal stylet length 106 that is generally straight and non-self-coiling. The distal end tip 108 is configured with a sharp, tissue-piercing beveled geometry. In other embodiment, a piercing tip may be conical or otherwise configured to penetrate and/or cut into/through tissue. In still other embodiments, the tip may be rounded and generally atraumatic, but preferred embodiments are configured to complement the distal piercing/penetrating tip of a needle and/or to extend beyond a needle body to form a leading surface. It should specifically be noted that, as in certain other drawing figures, FIG. 1 is not to scale, and the relative size of the self-coiling loop 104 will be much larger (relative to the non-coiling end length(s)) in many embodiments than shown, and the stylet thickness/diameter will be much smaller (relative to length) than shown.

The memory material may include one or more shape-memory polymers such as, for example, PEEK (polyether ether ketone), polyurethane, polyethylene, PTFE (polytetrafluoroethylene), or nylon, and if the memory material includes metal, it may include an alloy selected from nickel-titanium, nickel-titanium-cobalt, nickel-titanium-chromium, nickel-titanium-niobium, nickel-titanium-hafnium, nickel-titanium-palladium, nickel-titanium-platinum, nickel-titanium-iron, nickel-titanium plus rare earth elements, iron-manganese-silicon, iron-platinum, iron-nickel, iron-nickel-cobalt, iron-nickel-cobalt-aluminum-tin-tantalum, cobalt-chromium, stainless steel, spring steel, and any combination thereof, including any combination of polymer(s) and/or metal(s). One preferred embodiment includes superelastic nickel-titanium (nitinol) wire. The methods of thermosetting or otherwise imposing a "memorized" shape onto memory-metal alloys and shape-memory polymers are well-known known in the art, and those of skill in the art will be enabled by the present disclosure and contemporary knowledge to configure stylets in keeping with the presently claimed invention embodiments. The intermediate self-coiling stylet length 104 may be configured to form one or more parallel and/or spiraling/concentric loops that have a circular, oval, elliptical, obround, and/or other rounded geometry. This intermediate self-coiling stylet length will effectively reduce the droop length of a stylet as compared to a stylet otherwise identical but lacking a self-coiling length. Otherwise stated, the presence of an intermediate self-coiling stylet length effectively limits a default droop length of a stylet. The default droop length is the otherwise-unconstrained straight-line length from a secured upper end of a stylet to a lower end thereof that is allowed to droop with gravity, which typically will be about the same as or only slightly less than the full length of a standard stylet.

The intermediate self-coiling stylet length 104 preferably will form the one or more loops with an outer diameter of about 5 cm to about 30 cm in certain embodiments, with a preference in some embodiments for an outer loop diameter of about 7 cm to about 20 cm. This will provide for the coiled stylet easily to be stored on the surface of one of the carts/trolleys commonly used in endoscopy operating suites without impeding the movement of personnel during the procedure and remaining conveniently accessible for re-use if/as needed.

The exact dimensions and proportions of different stylet embodiments may vary. For example, the length and outer stylet diameter (across a transverse section of the single-wire body) will be constructed and/or selected for compatibility with a particular needle. A stylet being used with a 25-gauge needle will have a different outer diameter than one for a 19-gauge or 22-gauge needle. Common lengths will be about 160 cm to about 190 cm. The outer diameter of the stylet 200 may range from about 0.012 inches (about 0.3 mm) to about 0.036 inches (about 0.9 mm), for stylet lengths ranging from about 850 mm to about 1850 mm.

One exemplary embodiment is a 170 cm long stylet having an outer diameter of about 0.035 inches (about 0.89 mm). This sample stylet embodiment includes an intermediate self-coiling length that is about 154 cm. It also includes a distal straight length of about 16 cm, terminating in a sharp/penetrating beveled tip, and its proximal length is not straight but is co-terminal with a proximal portion of the self-coiling intermediate length. This configuration provides for a desirable balance between the functional advantages of the unique self-coiling design and the provision of a non-self-coiling distal length that will behave predictably and uniformly (in contrast, for example, with the non-uniform behavior of a guidewire that will have at least a slight distal-end curvature as required for its desired steerability/navigability function). In other embodiments, a proximal length of an exemplary stylet may be straight.

In certain preferred embodiments, a generally straight distal stylet length is no more than about 10% of the complete stylet length. In certain preferred embodiments, the self-coiling intermediate length may include up to about 95% of the complete stylet length. In some embodiments, the self-coiling length may be about 80% to about 92% of the complete stylet length, with about 4% to about 9% of the complete length being a substantially straight distal length, and the remainder (if any) being a substantially straight proximal length.

The self-coiling length may be substantially co-planar along its length when coiled, which is to say that—with the exception of slight off-set for any lengthwise overlap—substantially the entire length of certain preferred embodiments of the stylet 100 lie along a single plane, with the slight off-set being related directly to the thickness/outer diameter of the stylet body (i.e., as needed because the stylet cannot intersect itself). For this and other embodiments, the description of being substantially co-planar along the self-coiling length is for a stylet resting unconstrained upon a flat/planar surface. However, a primary object of the presently disclosed embodiments is to provide a self-coiling stylet that will have a shorter effective length (e.g., from a port where it is being withdrawn from a catheter, needle, or other medical tube device to its proximal end, the position of which preferably can remain unconstrained other than by the self-coiling nature, without reaching the floor or another surface toward which it would normally tend based upon gravity and its mass and shape).

Figure 1A:
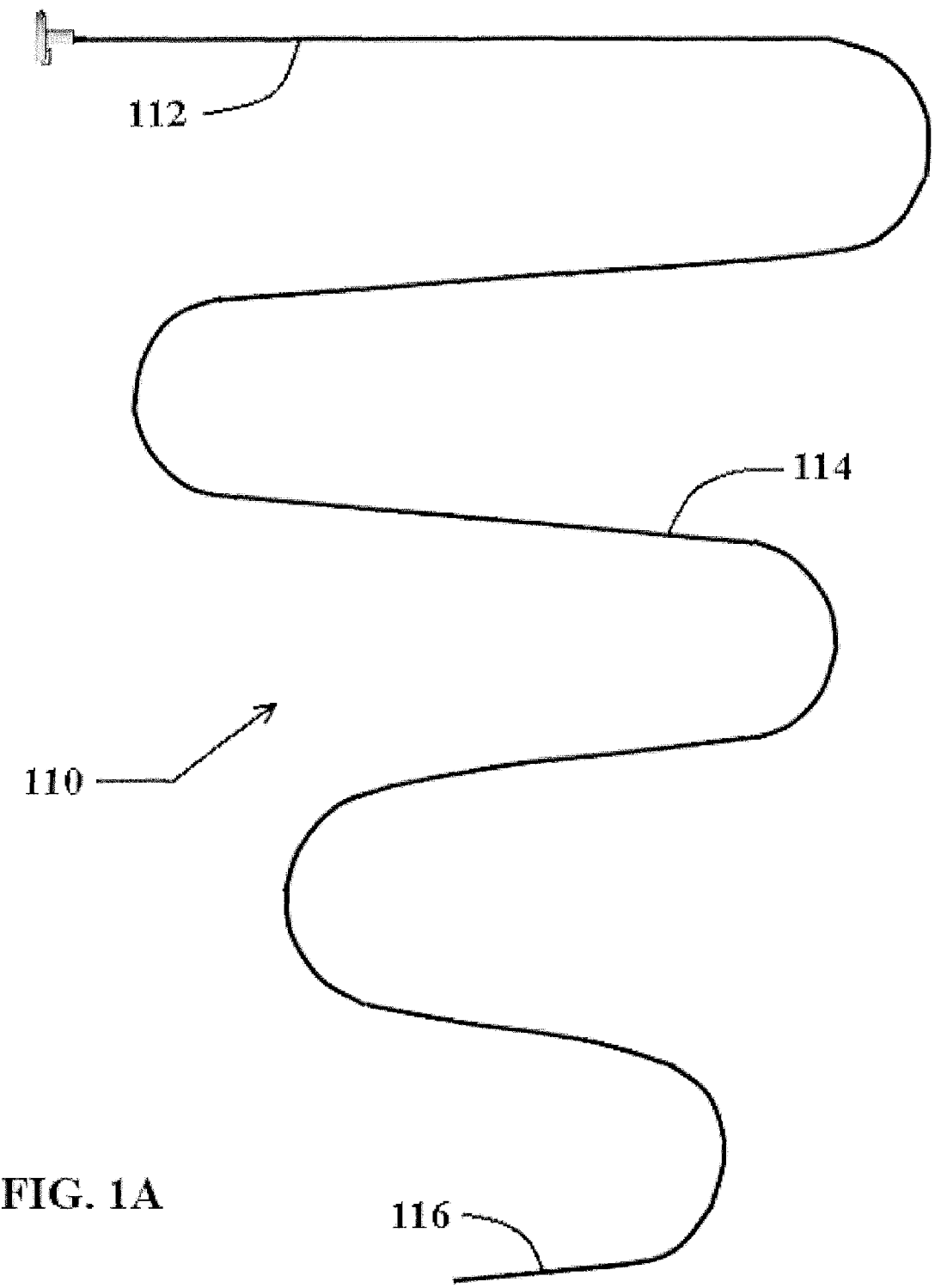

FIG. 1A shows a stylet 110 constructed with an elongate single-wire shape-memory material body with a complete length that includes a proximal stylet length 112, an intermediate self-coiling stylet length 114 including a plurality of sinuous curves that preferably are oriented/disposed along a single plane, and a distal stylet length 116 that is generally straight and non-self-coiling. The plurality of curves represented is purely exemplary, and actual embodiments may have more or fewer curves of similar or different proportionality. Some preferred embodiments may exclude sinuous curves of the type shown, the self-coiling/memory material nature of which is such that the stylet length does not loop back on itself in the manner of other embodiments presently described.

Figure 1B:
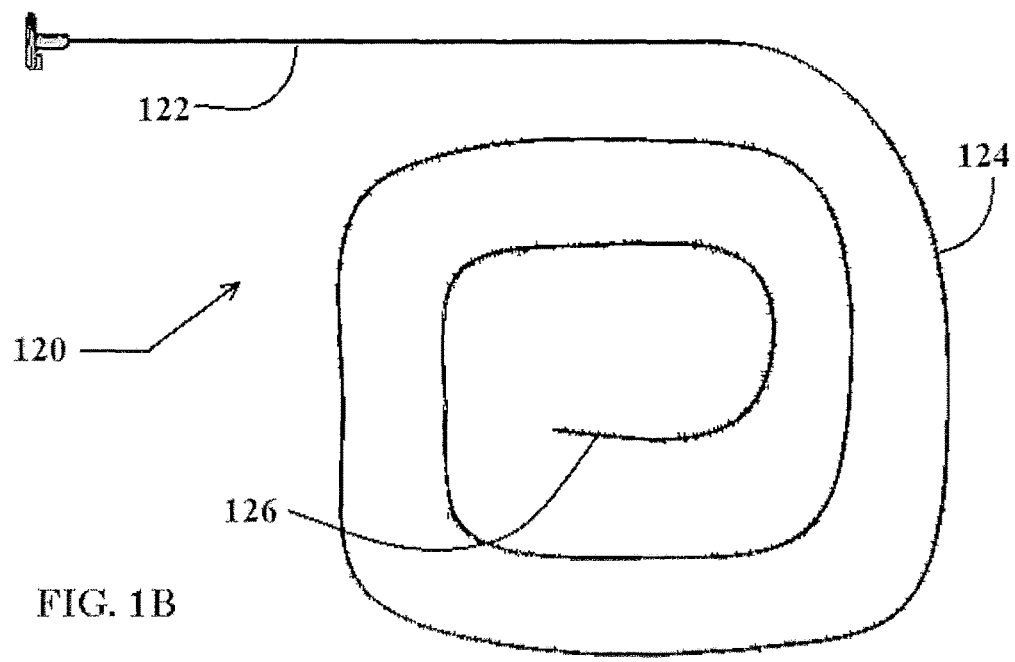
Figure 1C:
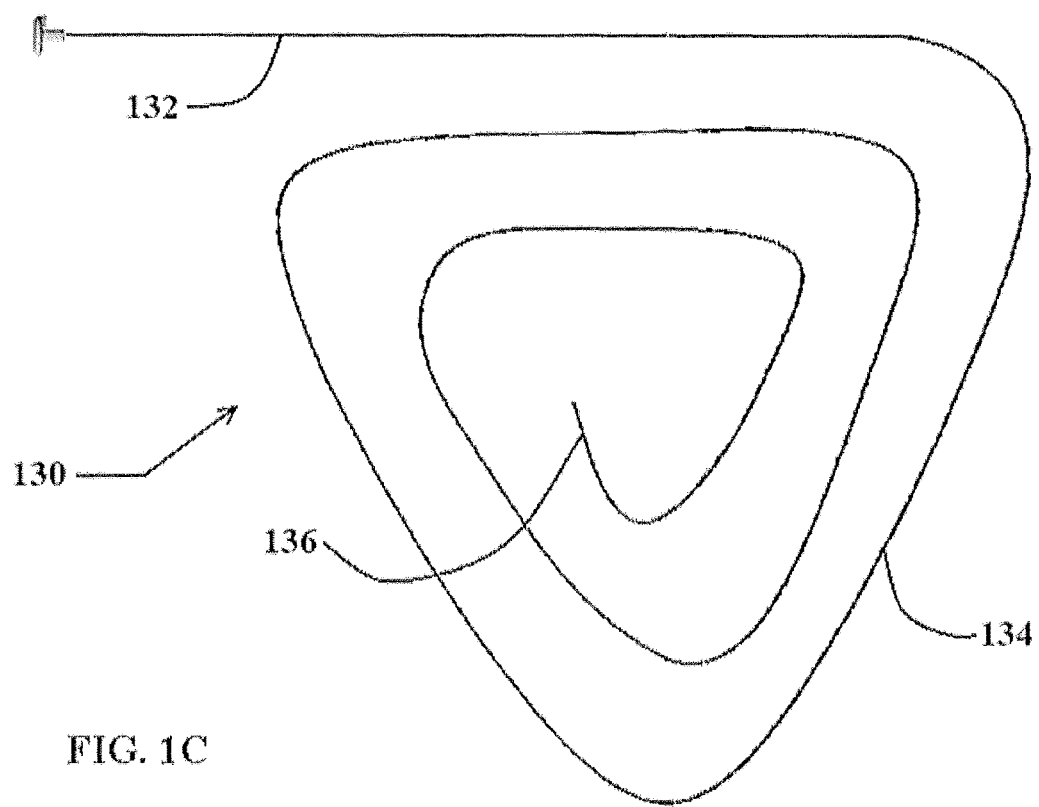

FIG. 1B shows a stylet 120 constructed with an elongate single-wire shape-memory material body with a complete length that includes a proximal stylet length 122, an intermediate self-coiling stylet length 124 including a plurality of generally concentric rounded-geometry shapes that preferably are oriented/disposed along a single plane, and a distal stylet length 126 that is generally straight and non-self-coiling. The generally concentric rounded-geometry shapes shown are generally rectangular, but—in other embodiments—they may be more square, rectangular, pentagonal, hexagonal, heptagonal, etc. For example, FIG. 1C shows a stylet 130 constructed with an elongate single-wire shape-memory material body with a complete length that includes a proximal stylet length 132, an intermediate self-coiling stylet length 134 including a plurality of generally concentric rounded-triangle shapes that preferably are oriented/disposed along a single plane, and a distal stylet length 136 that is generally straight and non-self-coiling.

Figure 1D:
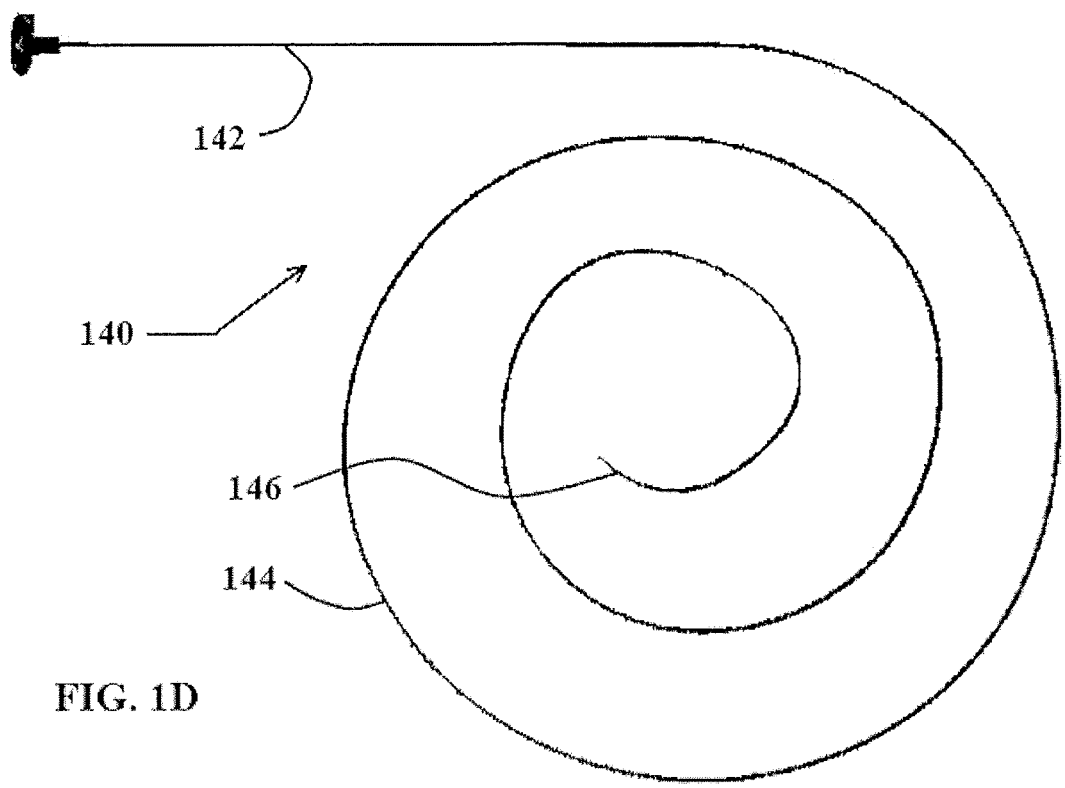
Figure 1E:
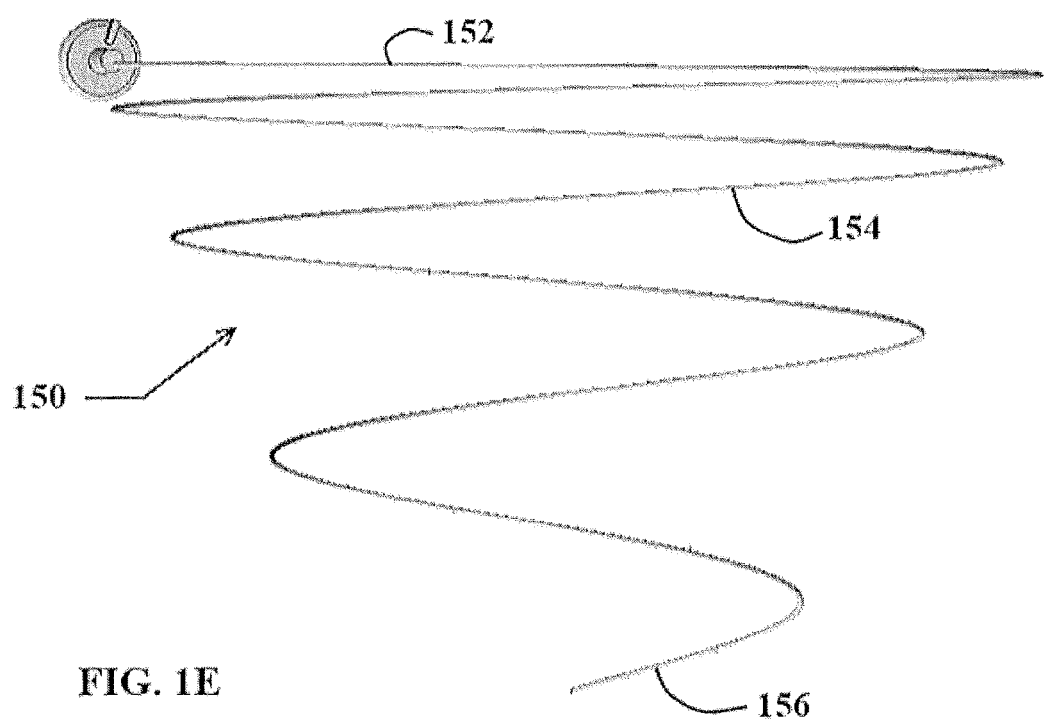

As another example of an embodiment, FIG. 1D shows a stylet 140 constructed with an elongate single-wire shape-memory material body with a complete length that includes a proximal stylet length 142, an intermediate self-coiling stylet length 144 including a plurality of generally concentric circular (or oval or other round) shapes that preferably are oriented/disposed along a single plane to form a planar spiral, and a distal stylet length 146 that is generally straight and non-self-coiling. In yet another embodiment, FIG. 1E shows a stylet 150 constructed with an elongate single-wire shape-memory material body with a complete length that includes a proximal stylet length 152, an intermediate self-coiling stylet length 154 including a plurality of generally concentric circular (or oval or other round) shapes that preferably are oriented/disposed outside of a single plane to form a rising spiral or helix, and may include a distal stylet length 156 that is generally straight and non-self-coiling.

Figure 1F:
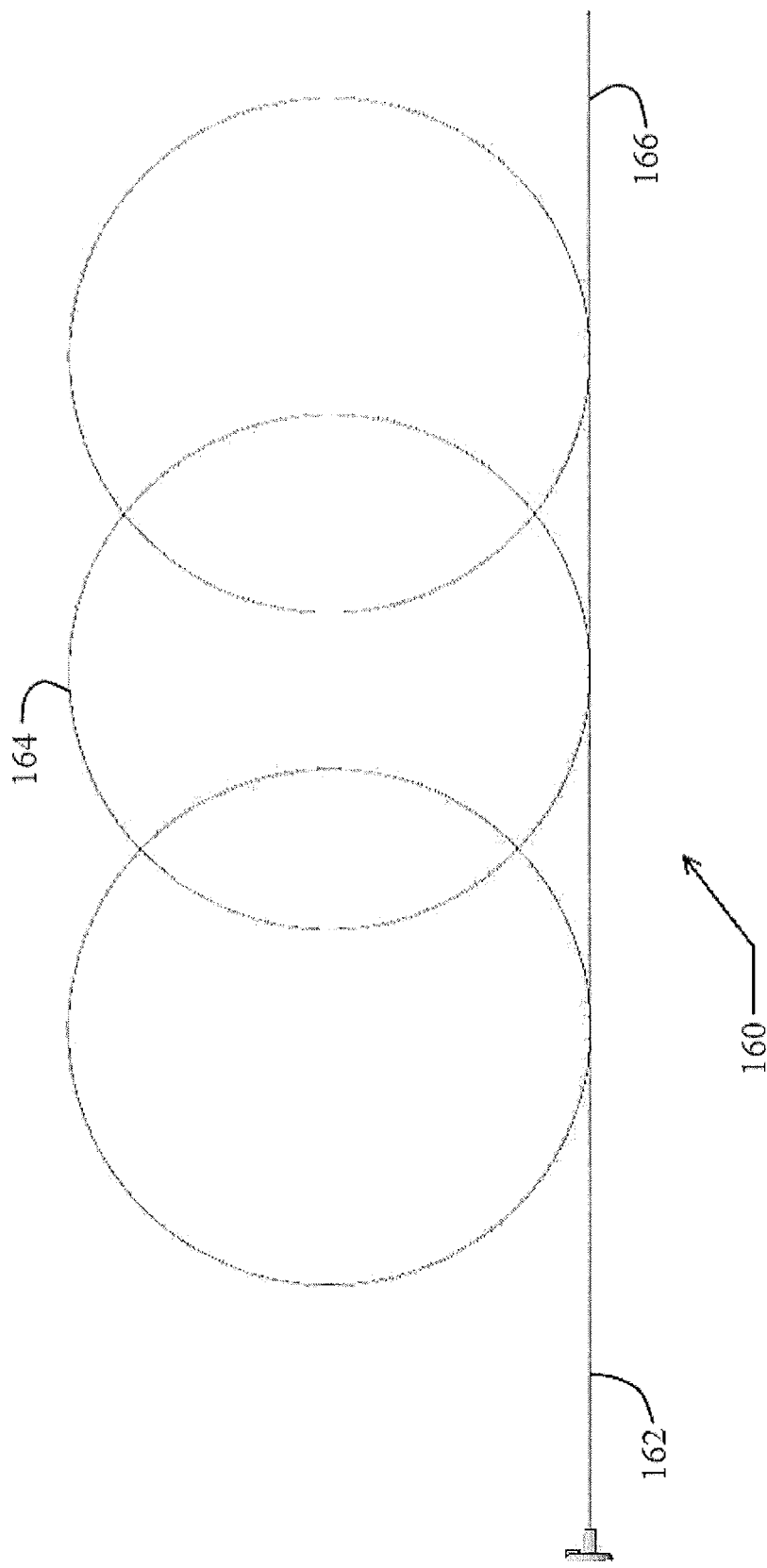

In a different embodiment, FIG. 1F shows a stylet 160 constructed with an elongate single-wire shape-memory material body with a complete length that includes a proximal stylet length 162, an intermediate self-coiling stylet length 164 including a plurality of generally or partially overlapping, non-concentric, circular (or oval or other round) loop shapes. These loops preferably are oriented/disposed substantially along a single plane to form a planar spiral, and a distal stylet length 166 is included, which may be generally straight and non-self-coiling. The illustrated embodiment includes three overlapping, non-concentric loops along the intermediate self-coiling stylet length 164, but other embodiments may have more or fewer such loops.

Figure 1G:
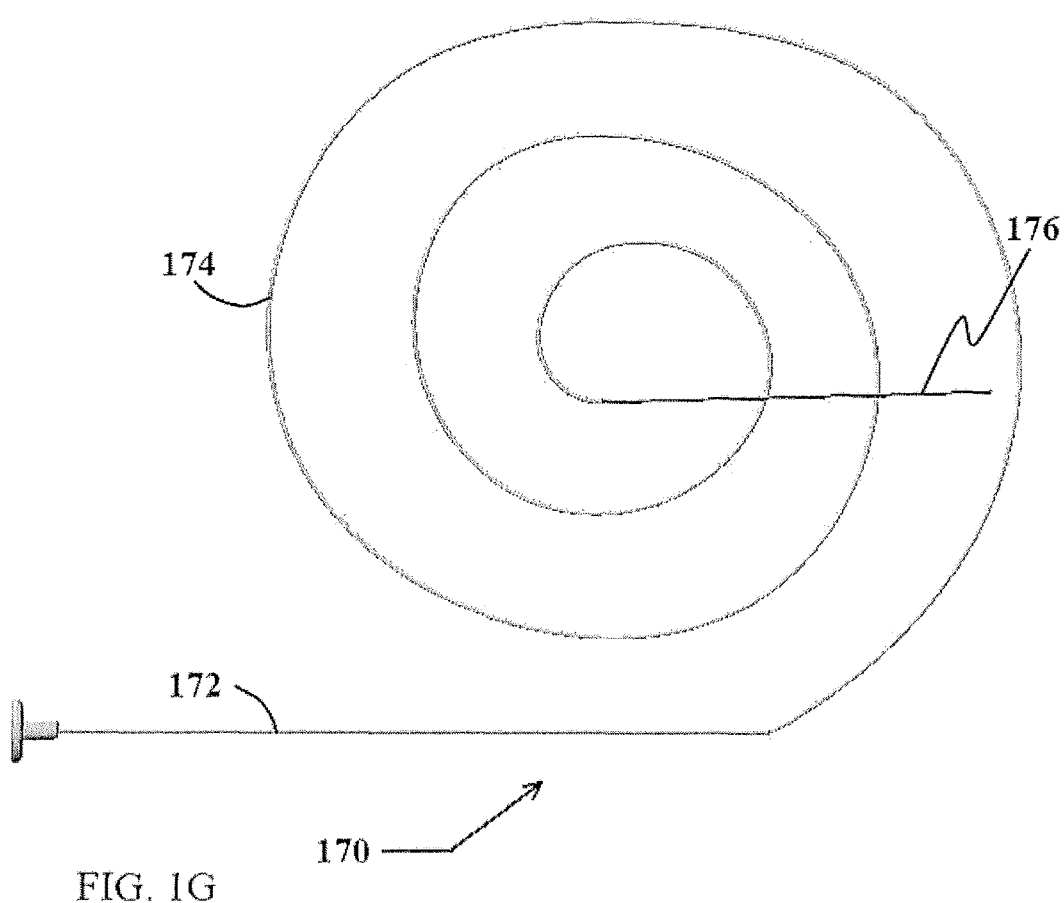
Figure 1H:
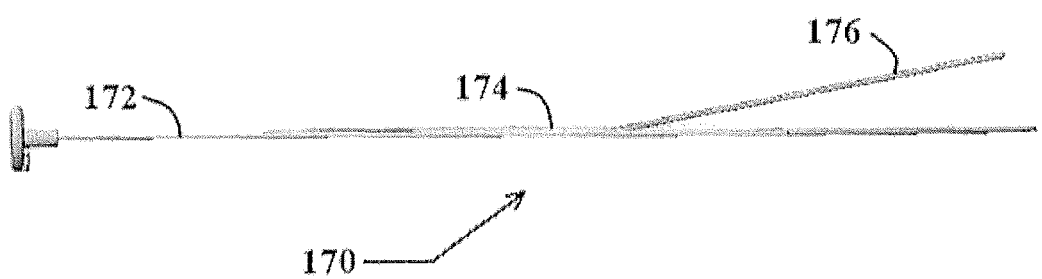

In a different embodiment, FIGS. 1G-1H show, respectively, plan and elevation views of a stylet 170 of the present disclosure. The stylet 170 constructed with an elongate single-wire shape-memory material body with a complete length that includes a proximal stylet length 172, an intermediate self-coiling stylet length 174 including a plurality of generally concentric circular (or oval or other round) loop shapes. These loops preferably are oriented/disposed substantially along a single plane to form a planar spiral. A distal stylet length 176 that is generally straight and non-self-coiling. The illustrated embodiment includes three overlapping, non-concentric loops along the intermediate self-coiling stylet length 174, but other embodiments may have more or fewer such loops. As shown most clearly in the elevation view of FIG. 1H, the distal stylet length 176 angles/extends up out of the plane generally defined by the concentrically-wound intermediate self-coiling stylet length 174.

Figure 2:
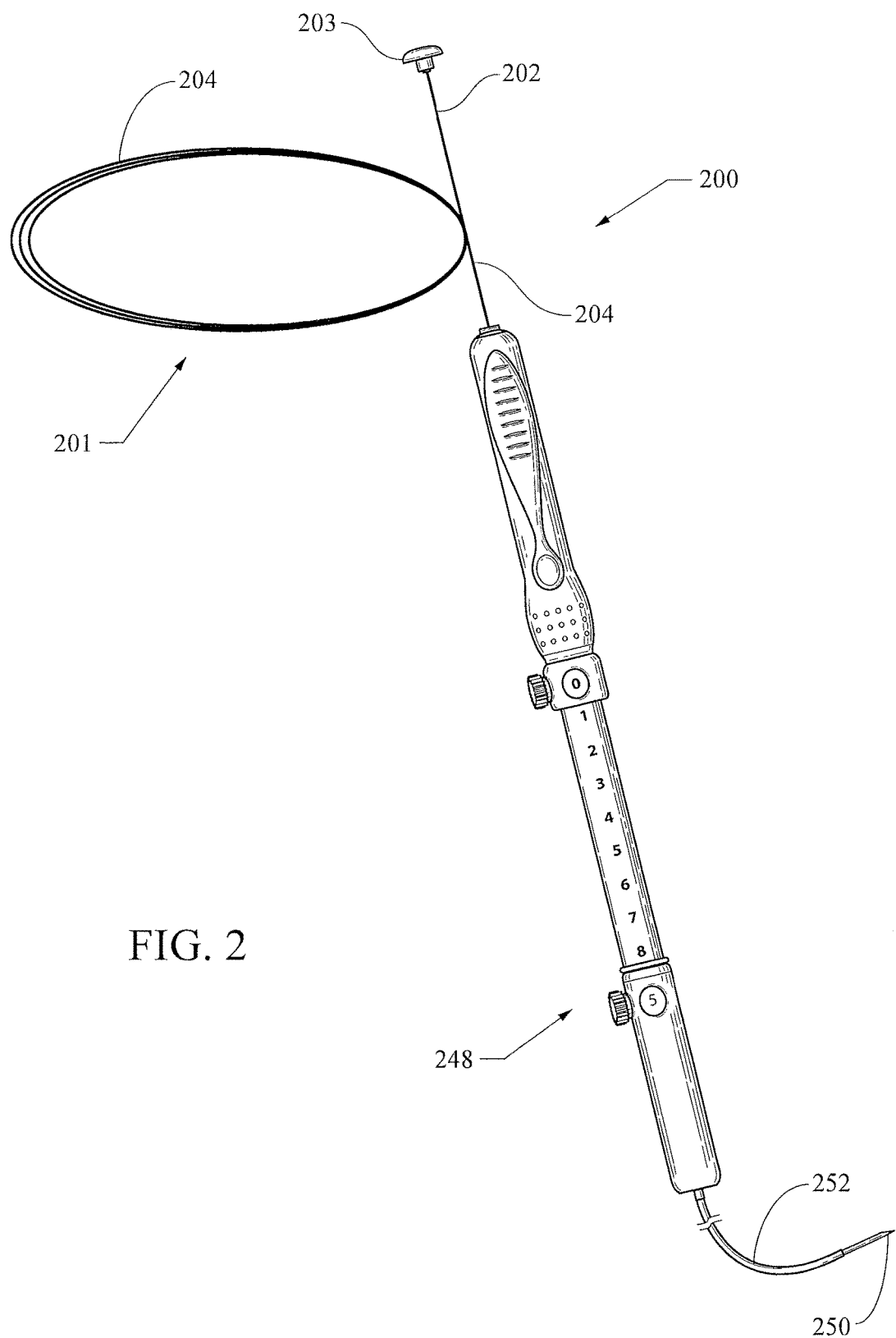
FIG. 2 shows a self-coiling single-wire-body stylet as part of a needle/stylet system embodiment.

FIG. 2 shows an embodiment of medical tube passage system in the form of a medical endoscopy needle and stylet system 200 including a needle 250 extending from a needle sheath 252 workably attached with a needle handle 248, and a self-coiling stylet 201. The stylet 201 is constructed with an elongate single-wire memory-metal body with a complete length that includes a proximal stylet length 202 terminating in a cap 203, a self-coiling intermediate stylet length 204, and a distal stylet length (not shown, disposed within the needle lumen). The stylet is shown as partially withdrawn from the lumen of the needle 250. The self-coiling intermediate stylet length 204 is shown as forming a generally oval spiral configuration, where each of the more proximal loops includes an outer diameter about the same as or slightly less than the immediately-more-distal adjacent loop. This configuration will prevent tangling during removal of the stylet 201 from the needle lumen and/or during reintroduction of the stylet 201 into that lumen. Although not shown, the self-coiling intermediate stylet length 204 extends through a significant length of the needle. It should be appreciated that the medical tube component embodied here as a needle may be any other medical tube device such as, for example, a catheter, introducer, sphincterotome, or other tubular device including a lumen that houses or is configured to house a stylet. Stylets of the present disclosure most preferably will be used with medical tube devices that will benefit (e.g., with respect to ease of use, navigability, and/or other structural or functional aspects) from the presence therein of a stylet that can be removed with efficient use of space and paucity of need for additional handling of withdrawn stylet length.

Other tangle-prevention features may include that the self-coiling intermediate length is thermoset or otherwise imposed with a shape configured to prevent tangling such as, for example, one or more of a helical construction with a slight pitch imparted to each of the coils, slightly-decreasing or increasing diameters and/or curvatures of each successive coil, and slightly differing shapes of the coils. Stated differently, a coil immediately adjacent to at least a first coil may be disposed at a slight pitch relative thereto, include a different coil diameter in at least one dimension, or any combination thereof effective to prevent—or at least minimize the risk of—tangling. As shown in FIG. 2, the moment of force of the stylet 201 is less than the moment of force of the needle 250, such that the self-coiling length of the stylet within the needle lumen does not deflect or impose any curvature upon the needle. Specifically, those of skill in the art will appreciate that the needle 250 inherently has a moment of force resisting curvature; this is overcome to varying degrees during use (e.g., navigating the needle through an endoscope working channel), but is—in the presently preferred embodiments—greater than the "pro-curvature/self-curving" moment of force of the stylet 201. Thus, as illustrated, the stylet 201 is disposed through a longitudinal lumen of the medical endoscopy needle 250, and the self-coiling stylet length 204 disposes the stylet to coil itself upon removal from the lumen by a person operating the needle system or assisting therewith.

The unique self-coiling feature presents several advantages for the present embodiments over existing stylets. For example, it helps reduce procedure time and activity level, because the nurse or other person who removes the stylet from the needle does not have to manually wind up, then hold, tangle, and/or clip the stylet to prevent it from whipping around, falling to the floor, or otherwise moving in a manner that will allow contamination and/or make it more difficult and time-consuming to reintroduce the stylet to the needle if needed. The presently disclosed configuration also reduces complexity and procedure time if the stylet needs reintroduced into the needle lumen (e.g., for the needle to be repositioned without inadvertent sample collection). In contrast with existing designs that require the handler to manually detangle, unclip, or otherwise unencumber the stylet and utilize both hands to feed the stylet back into the needle lumen, the present embodiments allow one-handed reintroduction into the needle with less time and less risk of the stylet flopping around and/or contacting surfaces that it should not.

Figure 2A:
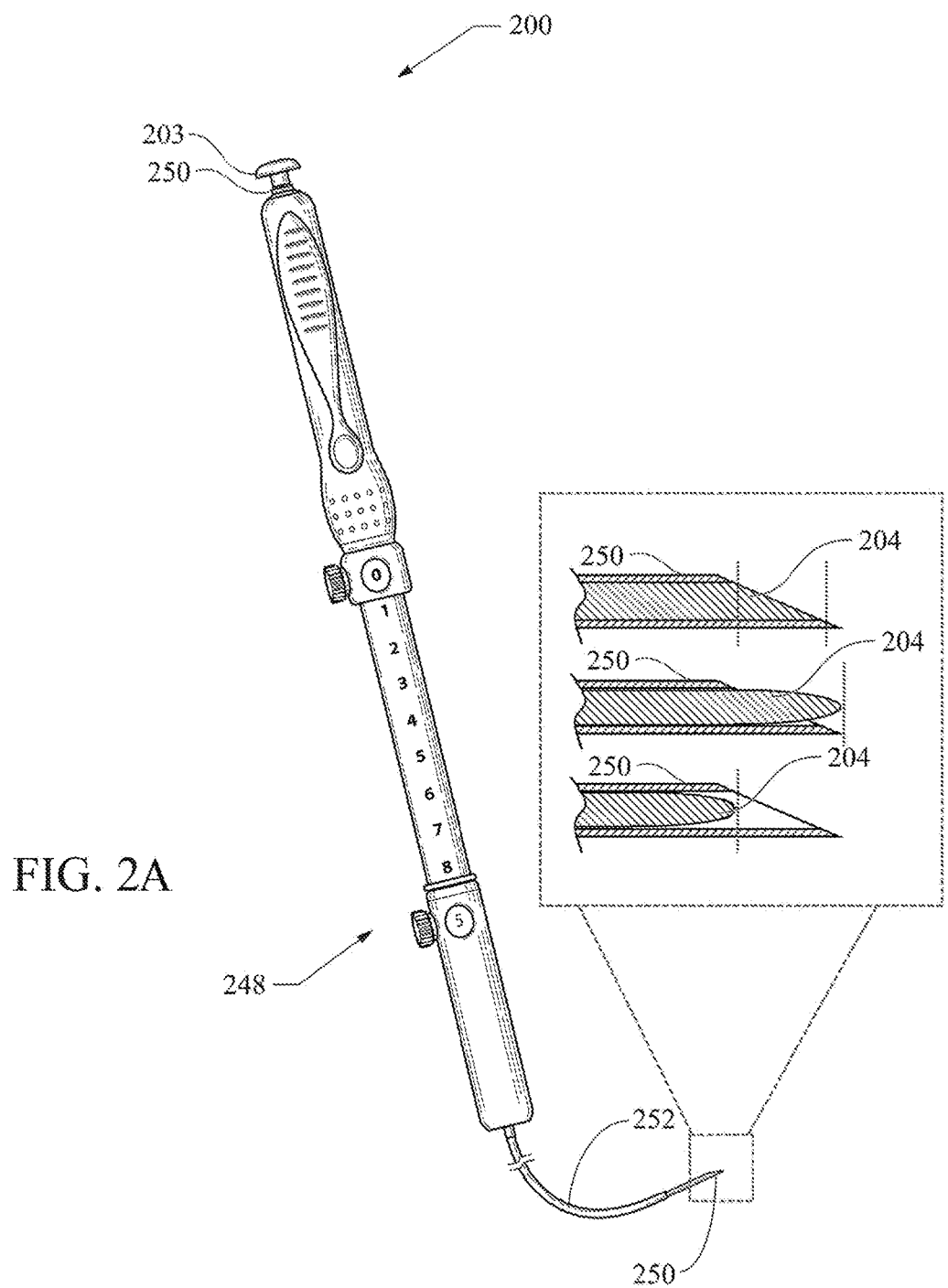
Figure 3A:
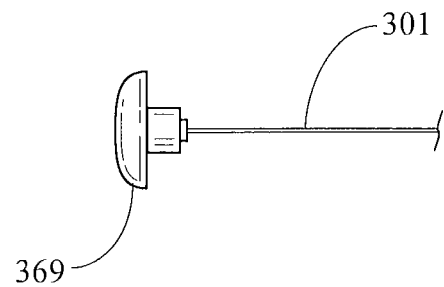
FIGS. 3A-3C show proximal end configuration embodiments of a self-coiling single-wire-body.
Figure 3B:
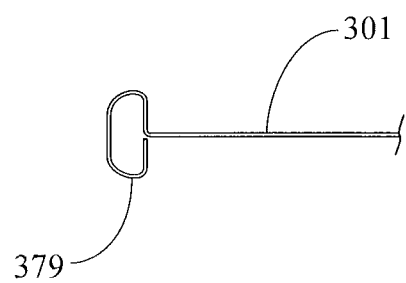
Figure 3C:
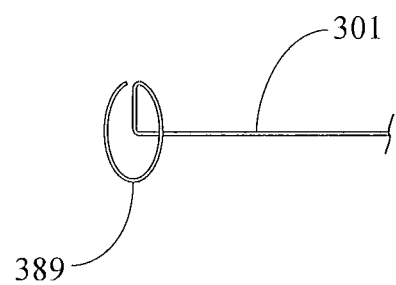

FIGS. 3A-3C illustrate configurations for the proximal end terminus of a stylet according to the present embodiments, each with a proximal stylet terminus portion that is larger in diameter (by effective outer profile) than the needle, with reference also to FIG. 2A for proximal and distal alignment/position of the stylet and a proximal-end portion thereof (where the stylet cap 203 in FIG. 2A can be replaced with the proximal end stylet region embodiments of FIGS. 3A-3C, each of which will contact a proximal end terminus of the needle 250 in the manner shown in FIG. 2A). FIG. 3A shows a configuration currently in use, with a proximal end region of a stylet 301 including a polymer stylet cap 369. The stylet cap 369 provides a broad proximal terminus for the stylet 301 that provides a handle for withdrawing the stylet 301 and prevents the proximal end of the stylet 301 from traveling into the needle lumen. This and other proximal-end structures may be used with self-coiling stylets of the present disclosure.

For example, as shown in FIG. 3B, a proximal stylet end structure 379 may be constructed as a loop including at least one portion that is generally perpendicular to the longitudinal axis of a stylet 301 and generally coplanar with an immediately adjacent stylet length. This proximal loop 379 may be configured as a handle. In one preferred embodiment, the loop 379 is disposed at a distance from a stylet distal end such that the generally perpendicular transition of the loop 379 to the rest of the stylet 301 will align with and contact the proximal end of a needle 250 when the distal stylet end aligns desirably relative to the needle's distal end. Examples of desirable alignments are shown in FIG. 2A, where a magnified call-out box shows three examples of ways in which a distal end of the stylet 204 may align with a distal end of a needle 250 when the proximal stylet terminus (e.g., 203, 369, 379, 389), contacts a proximal end terminus of the needle 250 at the top of the handle, with dotted lines used to illustrate the alignment of the distal-terminal end of the stylet with a distal-terminal end surface of the needle 250 (e.g., along one or more portions of the distal-end-terminal needle bevel, where those of skill in the art will appreciate that the top-most illustration in the FIG. 2A call-out box may be coterminal around an entire distal-end-terminal circumferential surface of the needle 250 so as to form coplanar termini of the needle and stylet).

Another example, shown in FIG. 3C, is a proximal stylet end structure 389 be constructed as a loop including at least one portion that is generally perpendicular to the longitudinal axis of a stylet 301, where the loop portion generally lies along a plane that is not coplanar with an immediately adjacent stylet length, and which plane may be perpendicular/transverse relative to the immediately adjacent stylet length. This proximal loop 389 may be configured as a handle. In one preferred embodiment, the loop handle 389 is disposed at a distance from a stylet distal end such that the generally perpendicular transition of the loop 389 to the rest of the stylet 301 will align with the proximal end of a needle (not shown) when the distal stylet end aligns desirably relative to the needle's distal end.

Experimental Data and Examples

Figure 4A:
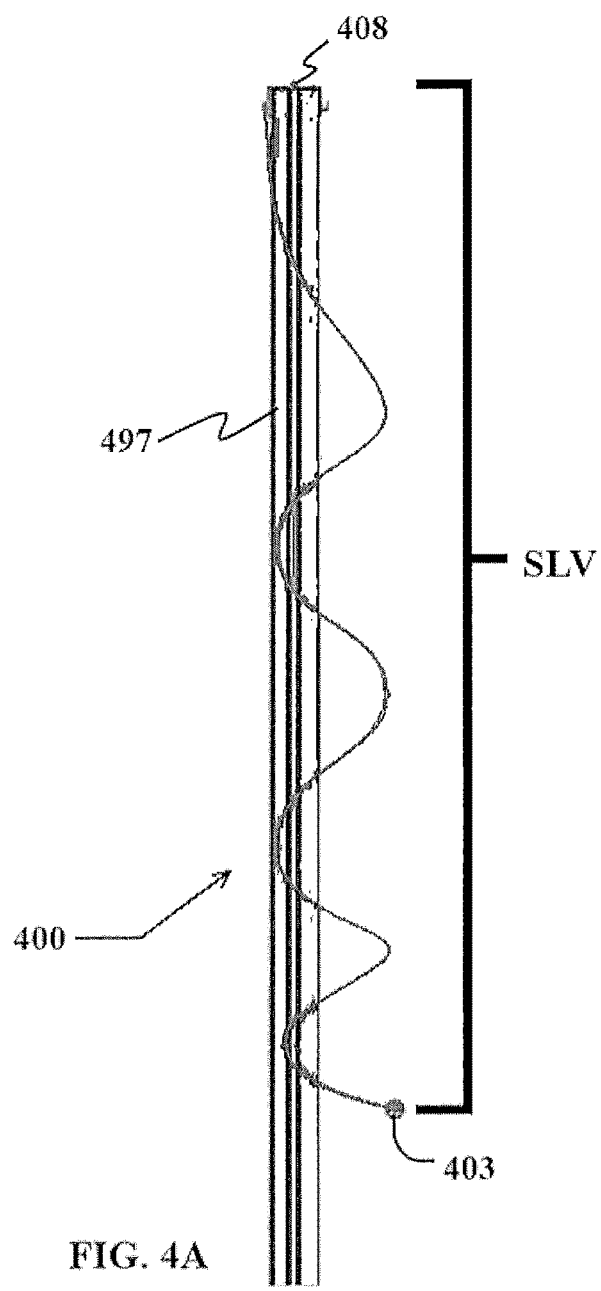
FIG. 4A shows a droop length measurement illustration.
Figure 4B:
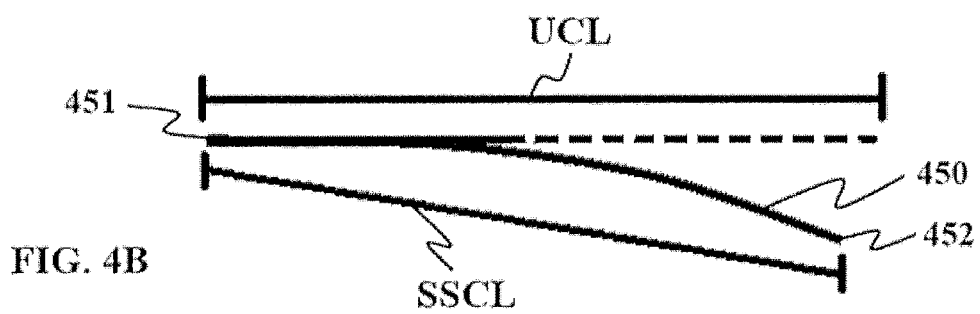
FIG. 4B shows, diagrammatically, a shape-set measurement illustration.

Examples of the efficacy of the present embodiments may be appreciated with reference to FIGS. 4A and 4B, as well as the following data. Table 1 through Table 5 show the experimental data for the needles identified therein. In each test, a closed-coil stylet 400 (configured with a self-coiling loop, as in FIG. 1) was directed longitudinally through the lumen of a needle 450. In each example of Tables 1-4, the stylet 400 was a heat-set nitinol stylet, 172 cm in length, placed through a stainless steel needle of the gauge identified, with the outer cross-sectional diameter of each stylet being about the same as the inner diameter of the needle identified. In Table 5, the stylet 400 was cold-worked nitinol. Cold worked nitinol is nitinol in a "cold work condition" (as drawn or as rolled), which has not been subjected to a final heat treatment (e.g., shape set anneal). In each example, the heat (or cold) set diameter of the stylet wire is provided in the leftmost column, which refers to the outer diameter of the generally circular loop(s) formed by the self-coiling portion of the stylet.

The droop length test was conducted as follows (with reference to FIG. 4A): a distal tip 408 of the coiled stylet 400 was fixed/held in a position at the upper end of a vertical support 497 that allowed the rest of the stylet 400 to drop freely, subject only to the same gravitational forces likely to be present in an operating suite during the time that a stylet is being withdrawn from a tubular device, and it is desirable to prevent it from drooping to the floor or otherwise moving around in the manner of a straight-wire—without requiring a person to capture and manually handle/wind-up/etc. the stylet. When the stylet 400 settled to a fully relaxed self-coiled length, the straight-line vertical distance (SLV) between the distal and proximal tip of the stylet was measured and recorded as droop length. This measurement did not include the stylet cap 403 shown at the bottom/proximal end of the stylet 400 in FIG. 4A.

The shape-set test was conducted as follows (with reference to FIG. 4B): the stylet 400 (not shown in FIG. 4B) was directed through the lumen of a stainless steel needle 450 of the gauge identified, such that a self-coiling intermediate length of the stylet occupied 100 cm of the needle's distal-most length, identified in FIG. 4B as the uncurved length (UCL; always 100 cm in these examples), measured from a proximal measuring-end 451 to the distal needle end 452.

Without the stylet present, the needle length was substantially straight-line as indicated by the dashed-line default/uncurved needle position in FIG. 4B. When the stylet was present, the curvature of its self-coiling intermediate length imposed a slight curve upon the needle 450, shown in solid line (not necessarily to scale). This is also shown in FIG. 4B, and the measure recorded for level of shape-set curve was the straight-line distance from the proximal measuring-end 451 (although not the actual proximal terminus of the full-length needle) of the now-curved needle 450, identified in FIG. 4B as the shape-set curved length (SSCL), which is a straight line across the opposite measuring points of the curved needle length. In each instance, the curvature imposed, if any, preferably will have little or no impact upon the pushability, trackability, and other navigability of a needle when a self-coiling stylet is present. The slight curvature imposed may provide a degree of directionality/steerability when operating the needle with stylet through an endoscope (such as, for example, a gastrointestinal endoscope—whether end-viewing, or side-viewing).

TABLE 1

19 ga Stylet (0.030" ± 0.0005 OD)

| Heat set Diameter of Stylet Wire (mm) | Droop Length (cm) | Level of shape set on 100 cm section of 19 ga needle cannula (cm) |
|---|---|---|
| 50 | 6 | 25.2 |
| 100 | 22 | 65.5 |
| 150 | 39 | 77.2 |
| 200 | 64.2 | 86.7 |
| 250 | 78.7 | 90.9 |

TABLE 2

20 ga Stylet (0.0245" ± 0.0005 OD)

| Heat set Diameter of Stylet Wire (mm) | Droop Length (cm) | Level of shape set on 100 cm section of 20 ga needle cannula (cm) |
|---|---|---|
| 50 | 10 | 51.3 |
| 100 | 28.5 | 73.5 |
| 150 | 48.3 | 81.8 |
| 200 | 79 | 89.2 |
| 250 | 98 | 92 |

TABLE 3

22 ga Stytet (0.016" ± 0.0005 OD)

| Heat set Diameter of Stylet Wire (mm) | Droop Length (mm) | Level of shape set on 100 cm section of 22 ga needle cannula (cm) |
|---|---|---|
| 50 | 16.6 | 89.3 |
| 100 | 49.5 | 95 |
| 150 | 84.8 | 97.7 |
| 200 | 110.3 | 98.2 |

TABLE 4

25 ga Stylet (0.012" ± 0.0005 OD)

| Heat set Diameter of Stylet Wire (mm) | Droop Length (cm) | Level of shape set on 100 cm section of 25 ga needle cannula (cm) |
|---|---|---|
| 50 | 29 | 94.8 |
| 100 | 77 | 97.7 |

TABLE 4-continued 25 ga Stylet (0.012" ± 0.0005 OD)

| Heat set Diameter of Stylet Wire (mm) | Droop Length (cm) | Level of shape set on 100 cm section of 25 ga needle cannula (cm) |
|---|---|---|
| 150 | 119.2 | 98.3 |
| 200 | 137.8 | 99.3 |

TABLE 5

25 ga Stylet (0.012" ± 0.0005 OD)

| Cold set Diameter of Stylet Wire (mm) | Droop Length (cm) | Level of shape set on 100 cm section of 25 ga needle cannula (cm) |
|---|---|---|
| 50 | 22 | 84 |
| 100 | 63 | 95 |

As shown in each of the examples, a larger-diameter loop size reduces the amount of shape-set impact upon a length of needle. Also, a smaller-diameter loop reduces droop length significantly, which will increase the ease of handling a stylet during withdrawal and reduce the likelihood of requiring additional hands to manage it as well as reduce the likelihood of it contacting surfaces it preferably should not.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A medical tube passage system with stylet, the system comprising:
   a medical endoscopy needle including at least one longitudinal needle lumen extending through a length thereof; and
   an elongate single-wire stylet body, removably disposed at least partially within the at least one longitudinal needle lumen, with a complete stylet body length equal to or less than a complete needle length measured from a proximal stylet terminus portion to a distal stylet end that aligns with a distal end of the needle when the proximal stylet terminus portion contacts a proximal end terminus of the needle, where the complete stylet body length includes
   a non-self-coiling proximal stylet length,
   an intermediate self-coiling shape-memory material stylet length that disposes the stylet to coil itself upon removal from the lumen, and a generally straight non-self-coiling distal-most stylet length;
  where the intermediate self-coiling stylet length effectively limits a default droop length of, and decreases a tangling risk of, the stylet body that is outside of the needle lumen; and
  where a diameter of the proximal stylet terminus portion is larger than a diameter of the needle and thereby prevents a proximal end of the elongate single-wire stylet body from traveling into the needle lumen, and where the proximal stylet terminus portion contacts the proximal terminus of the needle when the distal stylet end aligns with the distal end of the needle, and where the proximal stylet terminus portion is structurally configured as a proximal stylet handle with at least one portion that is both generally perpendicular and transverse to a longitudinal axis of the stylet, the longitudinal axis extending along a length of the stylet body disposed immediately adjacent the proximal stylet terminus portion.

2. The system of claim 1, where the shape-memory material comprises a polymer selected from PEEK, polyurethane, polyethylene, PTFE, nylon, a metal material selected from nickel-titanium, nickel-titanium-cobalt, nickel-titanium-chromium, nickel-titanium-niobium, nickel-titanium-hafnium, nickel-titanium-palladium, nickel-titanium-platinum, nickel-titanium-iron, nickel-titanium plus rare earth elements, iron-manganese-silicon, iron-platinum, iron-nickel, iron-nickel-cobalt, iron-nickel-cobalt-aluminum-tin-tantalum, stainless steel, spring steel, and any combination of said polymer(s) and/or metal material(s).

3. The system of claim 1, where the intermediate self-coiling stylet length forms one or more coils having an outer diameter of about 7 cm to about 30 cm.

4. The system of claim 1, where the generally straight non-self-coiling distal most stylet length is at least 4%, and no more than about 10% of the complete stylet body length.

5. The system of claim 1, where the intermediate self-coiling stylet length comprises about 80% to about 95% of the complete length.

6. The system of claim 1, comprising the complete stylet body length of about 180 cm, the generally straight non-self-coiling distal-most stylet length of about 2 cm to about 20 cm, and the non-self-coiling proximal stylet length of about 5 cm to about 14 cm.

7. The system of claim 1, where the distal stylet end is configured as a sharp, beveled tip.

8. The system of claim 1, where the proximal stylet terminus portion is structured as a loop.

9. The system of claim 1, where the intermediate self-coiling stylet length, when unconstrained, forms a plurality of coils as a spiral wherein each coil has substantially the same outer diameter.

10. The system of claim 1, where the intermediate self-coiling stylet length, when unconstrained, forms a plurality of coils as a spiral wherein each coil has a smaller outer diameter than a more proximal adjacent coil, and the coil outer diameters decrease likelihood of tangling or binding of the unconstrained stylet length.

11. The system of claim 1, where at least one coil of the intermediate self-coiling stylet length, when unconstrained, forms at least one coil shaped as a generally circular, generally elliptical, generally oval, or generally obround shape.

12. The system of claim 11, where a coil immediately adjacent to the at least one coil is disposed at a slight pitch relative thereto, includes a different coil diameter in at least one dimension, or any combination thereof.

13. The system of claim 1, where the default droop length of the stylet body that is outside of the needle lumen is such that a complete droop length of the stylet body is less than or equal to approximately 80% of the complete stylet body length.

14. A medical tube passage system with stylet, the system comprising:
  a medical endoscopy needle including at least one longitudinal needle lumen extending through a length thereof; and
  an elongate single-wire stylet body, removably disposed at least partially within the at least one longitudinal needle lumen, with a complete stylet body length equal to or less than a complete needle length measured from a proximal stylet terminus portion to a distal stylet end that aligns with a distal end of the needle when the proximal stylet terminus portion contacts a proximal end terminus of the needle, where the complete stylet body length includes
    a non-self-coiling proximal stylet length,
    an intermediate self-coiling shape-memory material stylet length that disposes the stylet to coil itself upon removal from the lumen, and
  a generally straight non-self-coiling distal-most stylet length;
    where the intermediate self-coiling stylet length effectively limits a default droop length of, and decreases a tangling risk of, the stylet body that is outside of the needle lumen, and where the inherent moment of force of the intermediate self-coiling stylet length is less than a moment of force inherent to the medical endoscopy needle that is resistant to a self-coiling force of the stylet body and where the intermediate self-coiling stylet length, when unconstrained, forms a plurality of coils as a spiral wherein each coil has a smaller outer diameter than a more proximal adjacent coil, and the coil outer diameters decrease likelihood of tangling or binding of the unconstrained stylet length; and
  where a diameter of the proximal stylet terminus portion is larger than a diameter of the needle and thereby prevents a proximal end of the elongate single-wire stylet body from traveling into the needle lumen, and where the proximal stylet terminus portion contacts the proximal terminus of the needle when the distal stylet end aligns with the distal end of the needle, and where the proximal stylet terminus portion is structurally configured as a proximal stylet handle with at least one portion that is both generally perpendicular and transverse to a longitudinal axis of the stylet, the longitudinal axis extending along a length of the stylet body disposed immediately adjacent the proximal stylet terminus portion.

15. A medical tube passage system with stylet, the system comprising:
  a medical endoscopy needle including at least one longitudinal needle lumen extending through a length thereof; and
  an elongate single-wire stylet body, removably disposed at least partially within the at least one longitudinal needle lumen, with a complete stylet body length equal to or less than a complete needle length measured from a proximal stylet terminus portion to a distal stylet end that aligns with a distal end of the needle when the proximal stylet terminus portion contacts a proximal end terminus of the needle, where the complete stylet body length includes a non-self-coiling proximal stylet length, an intermediate self-coiling shape-memory material stylet length that disposes the stylet to coil itself upon removal from the lumen, where at least one coil of the intermediate self-coiling stylet length, when unconstrained, forms at least one coil shaped as a generally circular, generally elliptical, generally oval, or generally obround shape, and where a coil immediately adjacent to the at least one coil is disposed at a slight pitch relative thereto, includes a different coil diameter in at least one dimension, or any combination thereof, and a generally straight non-self-coiling distal-most stylet length;

where the intermediate self-coiling stylet length effectively limits a default droop length of, and decreases a tangling risk of, the stylet body that is outside of the needle lumen, where the inherent moment of force of the intermediate self-coiling stylet length is less than a moment of force inherent to the medical endoscopy needle that is resistant to a self-coiling force of the stylet body; and where a diameter of the proximal stylet terminus portion is larger than a diameter of the needle and thereby prevents a proximal end of the elongate single-wire stylet body from traveling into the needle lumen, and where the proximal stylet terminus portion contacts the proximal terminus of the needle when the distal stylet end aligns with the distal end of the needle, and where the proximal stylet terminus portion is structurally configured as a proximal stylet handle with at least one portion that is both generally perpendicular and transverse to a longitudinal axis of the stylet, the longitudinal axis extending along a length of the stylet body and disposed immediately adjacent the proximal stylet terminus portion.

* * * * *